United States Patent
Fujiwara

(10) Patent No.: US 11,678,139 B2
(45) Date of Patent: Jun. 13, 2023

(54) TRAVELING DIRECTION DETERMINATION DEVICE, MOBILE DEVICE, AND TRAVELING DIRECTION DETERMINATION METHOD

(71) Applicant: LAPIS Semiconductor Co., Ltd., Yokohama (JP)

(72) Inventor: Kazunori Fujiwara, Yokohama (JP)

(73) Assignee: LAPIS SEMICONDUCTOR CO., LTD., Yokohama (JP)

( * ) Notice: Subject to any disclaimer, the term of this patent is extended or adjusted under 35 U.S.C. 154(b) by 33 days.

(21) Appl. No.: 17/191,093

(22) Filed: Mar. 3, 2021

(65) Prior Publication Data

US 2021/0289322 A1 Sep. 16, 2021

(30) Foreign Application Priority Data

Mar. 10, 2020 (JP) .............................. JP2020-041404

(51) Int. Cl.
*H04W 4/02* (2018.01)
*G01C 21/16* (2006.01)

(52) U.S. Cl.
CPC ............ *H04W 4/026* (2013.01); *G01C 21/16* (2013.01); *H04W 4/027* (2013.01)

(58) Field of Classification Search
CPC ....... H04W 4/026; H04W 4/027; G01C 21/16
See application file for complete search history.

(56) References Cited

U.S. PATENT DOCUMENTS

| | | | | |
|---|---|---|---|---|
| 2011/0306304 A1* | 12/2011 | Forutanpour | ..... | H04M 1/72457 455/67.11 |
| 2013/0046505 A1* | 2/2013 | Brunner | ................ | G01C 22/006 702/141 |
| 2013/0095861 A1* | 4/2013 | Li | .......................... | H04W 4/029 455/456.6 |
| 2017/0030717 A1* | 2/2017 | Azami | ..................... | G01S 19/49 |
| 2017/0105098 A1* | 4/2017 | Cordova | .................. | H04W 4/38 |
| 2019/0195636 A1* | 6/2019 | Imoto | ..................... | G01C 21/16 |
| 2021/0255211 A1* | 8/2021 | Szilágyi | .................. | G01P 13/00 |
| 2022/0113366 A1* | 4/2022 | Pipelidis | ............... | G01S 5/0278 |

FOREIGN PATENT DOCUMENTS

| JP | 2005-017308 A | 1/2005 |
|---|---|---|
| JP | 2012-168004 A | 9/2012 |
| JP | 5155117 B2 | 2/2013 |

* cited by examiner

*Primary Examiner* — Ernest G Tacsik
(74) *Attorney, Agent, or Firm* — Rabin & Berdo, P.C.

(57) ABSTRACT

Provided is a traveling direction determination device that determines, using an acceleration sensor that generates acceleration signals indicating acceleration in three axial directions together with a direction of the acceleration, a traveling direction of a moving object mounted with the acceleration sensor, the traveling direction determination device comprising a determination unit that executes a first determination process in which the determination unit selects, using the acceleration signals, any of the three axes as a gravity axis, the gravity axis being closest to an actual gravity direction of the moving object to determine a gravity direction of the moving object and a second determination process in which the determination unit selects either of the two axes excluding the axis selected as the gravity axis, as a travel axis, the travel axis being closest to an actual traveling direction of the moving object based on moving average values of the acceleration signals to determine the traveling direction of the moving object.

9 Claims, 6 Drawing Sheets

<1> [MOTION 1]
DEVICE INCLINES FORWARD

STANDING UP FROM CHAIR AND SITTING DOWN IN CHAIR

<2> [MOTION 2]
DEVICE INCLINES FORWARD

PICKING UP OBJECT ON FLOOR

<3> [MOTION 3]
DEVICE INCLINES FORWARD

SLIPPING ON SHOES WHILE STANDING

<1> [MOTION 1] DEVICE INCLINES FORWARD

STANDING UP FROM CHAIR AND SITTING DOWN IN CHAIR

<2> [MOTION 2] DEVICE INCLINES FORWARD

PICKING UP OBJECT ON FLOOR

<3> [MOTION 3] DEVICE INCLINES FORWARD

SLIPPING ON SHOES WHILE STANDING

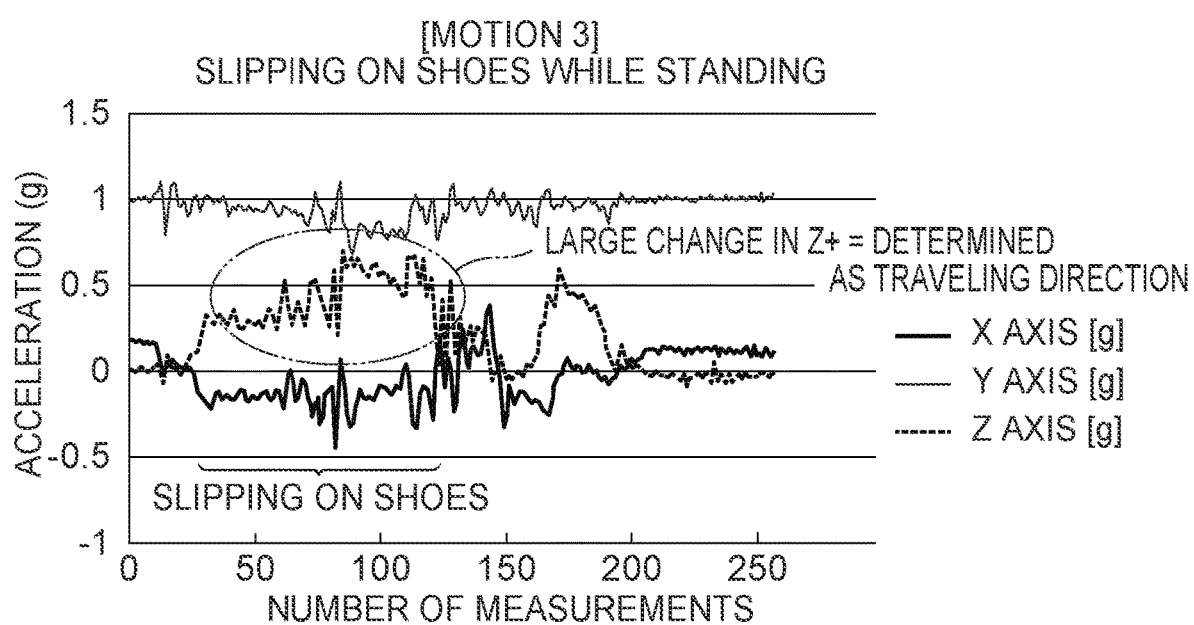

TRAVELING DIRECTION DETERMINATION DEVICE, MOBILE DEVICE, AND TRAVELING DIRECTION DETERMINATION METHOD

CROSS-REFERENCE TO RELATED APPLICATION

This application is based on and claims priority under 35 USC 119 from Japanese Patent Application No. 2020-041404 filed on Mar. 10, 2020, the disclosure of which is incorporated by reference herein.

BACKGROUND

Technical Field

This disclosure relates to a traveling direction determination device, a mobile device, and a traveling direction determination method.

Conventionally, pedestrian dead reckoning (PDR) has been known as a technique that applies mobile devices. PDR requires technology that accurately positions the moving distance of a person. For example, in the field of navigation technology, sensor functions such as acceleration, geomagnetism, and angular velocity that smartphones (hereinafter called "mobile phone devices"), which are an example of mobile devices, have are utilized to calculate the moving direction and the moving distance of a pedestrian and display the position of the pedestrian on a map. In such technical fields using mobile devices, technologies that determine directions such as the orientation of the mobile device or the moving direction of the person carrying the mobile device are essential technologies.

Concerning a technology that determines direction in the application of a mobile device, Japanese Patent No. 5,155,117 discloses a gravity axis determination apparatus for determining and detecting one of three axes constructing a three-dimensional space as a gravity axis, the gravity axis determination apparatus including: a signal generating part for generating at least two axis acceleration signals each indicating an acceleration in each of directions of at least two axes among said three axes; a fetching part for fetching each of said axis acceleration signals as at least two axis acceleration data trains; and a determining and detecting part for comparing data values of said axis acceleration data trains in a same time zone, determining one of said three axes as said gravity axis, and generating a detection signal indicating said gravity axis, wherein when said determining and detecting part determines a plurality of times with lapse of time that said data value in one of said axis acceleration data trains is larger than said data value of the axis acceleration data train other than said one of said axis acceleration data trains in said same time zone, the axis corresponding to said one of said axis acceleration data trains is determined as said gravity axis.

Furthermore, concerning a technology that judges the direction of a moving object, Japanese Patent Application Laid-open (JP-A) No. 2005-017308 discloses a navigation system including: acceleration detecting means that has sensing directions in two directions 90° to each other and detects acceleration of a moving object; judging means that judges whether or not the moving object is moving forward; and setting means that sets, using the output of the acceleration detecting means in a case where it has been judged by the judging means that the moving object is moving forward, polarities in the front and rear direction and the left and right direction of the acceleration detecting means.

Moreover, concerning a technology that calculates the traveling direction of a pedestrian, JP-A No. 2012-168004 discloses a mobile device carried by a pedestrian and including an acceleration sensor that outputs triaxial acceleration data, a geomagnetic sensor that outputs triaxial geomagnetic data, and traveling direction deciding means that decides the traveling direction of the pedestrian from the acceleration data and the geomagnetic data, wherein the traveling direction deciding means includes: swing phase extracting means that extracts swing phase acceleration data using the acceleration data of each axis and resultant acceleration which is the square root of the sum of squares of the acceleration data of all axes; designated fraction acceleration acquiring means that acquires a designed fraction of acceleration data from the swing phase acceleration data; rightward/leftward vector calculating means that calculates a rightward/leftward vector U based on the designated fraction of swing phase acceleration data; and traveling direction calculating means that calculates the traveling direction using the rightward/leftward vector U, a gravity vector and a geomagnetic vector M.

Here, in pedestrian positioning technologies, depending on how the pedestrian carries the mobile device (e.g., expressed by the orientation of the mobile device with respect to the ground), the traveling direction seen from the perspective of the mobile device changes. Even if sensors and the like provided in the mobile device are used to determine the traveling direction of the mobile device using some method, unless the direction in which the pedestrian carries the mobile device is considered, the chance that the traveling direction of the pedestrian will be erroneously determined, such as determining the traveling direction of the pedestrian to be the opposite direction of the actual traveling direction of the pedestrian for example, cannot be excluded. In such cases, there is the phenomenon that accurate pedestrian positioning cannot be performed. Consequently, traveling direction determination devices capable of more accurately determining the traveling direction of a pedestrian (generally a moving object) carrying a mobile device have been in demand. Furthermore, it would be very convenient if the traveling direction could be simply determined using the acceleration sensor and the like mounted in the mobile device.

JP-A No. 2005-017308 and JP-A No. 2012-168004 have the following characteristics. JP-A No. 2005-017308 discloses judging, in regard to a moving object mounted with an acceleration sensor having sensing directions in two directions where one is the traveling direction and the other is a direction rotated 90° therefrom, the direction in which acceleration has been detected just after the moving object has started moving to be the traveling direction. However, although the traveling direction can be judged when the output of the acceleration sensor has been detected in only one direction, the traveling direction cannot be judged when the output of the acceleration sensor has been detected in both of two directions, so the mounting direction of the acceleration sensor by which the traveling direction can be judged ends up being limited. In JP-A No. 2012-168004, the traveling direction is computed and output using the resultant acceleration calculated based on the output signals of the acceleration sensor, so the computation amount increases.

SUMMARY

In view of the above circumstances, an embodiment of this disclosure relates to providing a traveling direction determination device, a mobile device, and a traveling direction determination method that can simply determine, using the output of an acceleration sensor, the traveling direction of a moving object mounted with the acceleration sensor irrespective of the mounting direction of the acceleration sensor.

In order to solve the above problem, a traveling direction determination device pertaining to this disclosure determines, using an acceleration sensor that generates acceleration signals indicating acceleration in three axial directions together with a direction of the acceleration, a traveling direction of a moving object mounted with the acceleration sensor, the traveling direction determination device comprising a determination unit that executes a first determination process in which the determination unit selects, using the acceleration signals, any of the three axes as a gravity axis, the gravity axis being closest to an actual gravity direction of the moving object to determine a gravity direction of the moving object and a second determination process, in which the determination unit selects either of the two axes excluding the axis selected as the gravity axis, as a travel axis, the travel axis being closest to an actual traveling direction of the moving object based on moving average values of the acceleration signals, to determine the traveling direction of the moving object.

In order to solve the above problem, a mobile device pertaining to this disclosure includes: an acceleration sensor that generates acceleration signals indicating acceleration in three axial directions together with a direction of the acceleration; and the traveling direction determination device.

In order to solve the above problem, a traveling direction determination method pertaining to this disclosure determines, using an acceleration sensor that generates acceleration signals indicating acceleration in three axial directions together with a direction of the acceleration, a traveling direction of a moving object mounted with the acceleration sensor, the traveling direction determination method comprising: a first step of selecting, using the acceleration signals from the acceleration sensor in a case in which the moving object has performed a predetermined behavior, any of the three axes as a gravity axis to determine a gravity direction of the moving object; and a second step of selecting, as a travel axis based on moving average values of the acceleration signals, either of the two axes excluding the gravity axis, to determine the traveling direction of the moving object.

According to the embodiment of this disclosure, there is the advantageous effect that it becomes possible to provide a traveling direction determination device, a mobile device, and a traveling direction determination method that can simply determine, using the output of an acceleration sensor, the traveling direction of a moving object mounted with the acceleration sensor irrespective of the mounting direction of the acceleration sensor.

BRIEF DESCRIPTION OF THE DRAWINGS

FIG. 2C is a graph showing acceleration signals of motions when the person carrying the mobile device mounted with the acceleration sensor slips on shoes while standing;

DETAILED DESCRIPTION

An embodiment of this disclosure will be described in detail below with reference to the drawings. In the following description, a configuration where the traveling direction determination device pertaining to this disclosure is mounted in a mobile device carried by a person is described as an example. In the traveling direction determination device, the mobile device, and the traveling direction determination method pertaining to this embodiment, an acceleration sensor mounted in the mobile device is utilized to determine how the person is carrying the mobile device, and the traveling directions of the mobile device and the person are combined to improve the accuracy of pedestrian positioning technology.

Figure 1A:
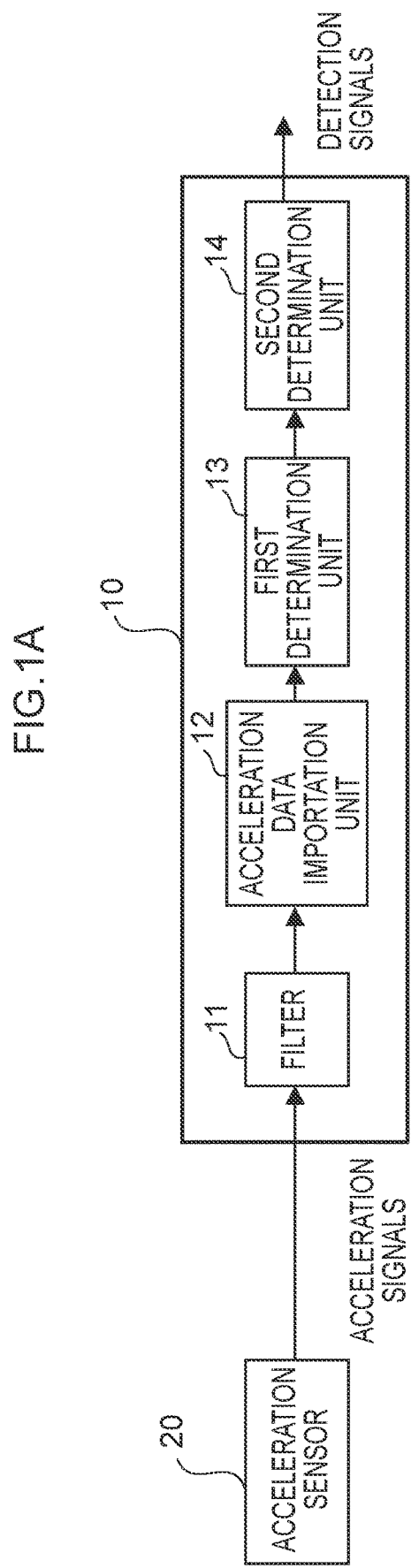
FIG. 1A is a block diagram showing an example of the configuration of a traveling direction determination device pertaining to an embodiment.

FIG. 1A is a block diagram showing, together with an acceleration sensor 20, an example of the configuration of a traveling direction determination device 10 pertaining to this embodiment. As shown in FIG. 1A, the traveling direction determination device 10 is configured to include a filter 11, an acceleration data importation unit 12, a first determination unit 13, and a second determination unit 14. The traveling direction determination device 10 is built into a mobile device, for example, and determines the traveling direction of a moving object in accordance with the orientation and inclination of the mobile device itself. The traveling direction determination device 10 pertaining to this embodiment can be configured using a microprocessor, for example, but it is not limited to this and may also be configured using an application-specific integrated circuit (ASIC) or discrete components. It will be noted that in this embodiment "mobile device" means mobile information devices in general, such as mobile phone devices, mobile personal computers (PCs), and personal digital assistants (PDAs). Furthermore, the "first determination unit 13" and the "second determination unit 14" are examples of a "determination unit" pertaining to this disclosure.

The acceleration sensor 20 is a triaxial acceleration sensor that generates, for each of an X axis, a Y axis, and a Z axis configuring a three-dimensional space, three axial acceleration signals indicating the magnitude and direction of acceleration on those axes. The acceleration sensor 20 is, for example, a micro-electromechanical systems (MEMS) acceleration sensor whose acceleration sensing mechanisms are fabricated by a semiconductor process. The sensing mechanisms of the MEMS acceleration sensor may be any of piezoresistive, capacitive, or thermal. As for its capacity, the MEMS acceleration sensor can measure a range of ±several g and can track fluctuations in acceleration from 0 Hz to about several hundred Hz.

Figure 1B:
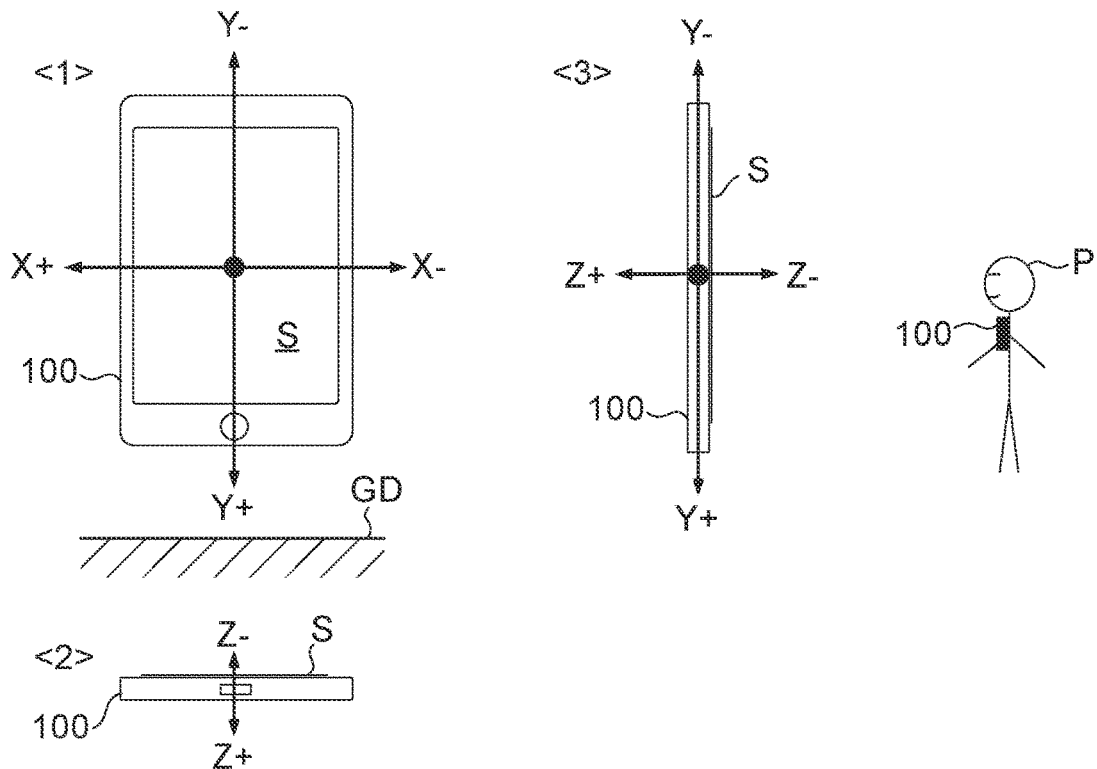
FIG. 1B is a drawing showing sensing directions of an acceleration sensor in a mobile device pertaining to the embodiment.

The acceleration sensor 20 generates axial acceleration signals showing signal levels in the range of ±1, for example, in regard to each of the X axis, the Y axis, and the Z axis. Namely, the direction of acceleration is indicated by ±, and the magnitude of acceleration is indicated by the absolute value of the signal level. The traveling direction determination device 10 is, for example, built into a mobile phone device 100 such as shown in FIG. 1B. In FIG. 1B the X axis and the Y axis are orthogonal to each other, with the Y axis corresponding to the longitudinal direction (lengthwise direction) of the mobile phone device 100 and the X axis corresponding to the transverse direction (widthwise direction) of the mobile phone device 100. The Z axis corresponds to the thickness direction of the mobile phone device 100 (a direction orthogonal to the X-Y plane). As shown in FIG. 1B, the mobile phone device 100 has a monitor screen S for displaying information and the like, and the direction of a normal with respect to the monitor screen S is the Z axis.

The acceleration sensor 20 outputs axial acceleration signals with signal levels according to the orientation (inclination) of the mobile phone device 100 that a carrier P carries. Regarding the X axis, the acceleration signal shows a "−" signal level when the right side of the mobile phone device 100 faces a ground GD shown in FIG. 1B<1> and shows a "+" signal level when the left side of the mobile phone device 100 faces the ground GD. Regarding the Y axis, the acceleration signal shows a "−" signal level when the top side of the mobile phone device 100 faces the ground GD and shows a "+" signal level when the bottom side of the mobile phone device 100 faces the ground GD. Regarding the Z axis, the acceleration signal shows a "−" signal level when the front side (the side with the monitor screen S) of the mobile phone device 100 faces the ground GD and shows a "+" signal level when the back side of the mobile phone device 100 faces the ground GD.

For example, in a case where the bottom side of the mobile phone device 100 is pointed toward the ground GD and fixed as shown in FIG. 1B<1>, the signal level on each of the X axis and the Z axis is 0 and the signal level on the Y axis is +1. Furthermore, in a case where the mobile phone device 100 is rotated 90° clockwise from the orientation shown in FIG. 1B<1> and fixed, the signal level on each of the Y axis and the Z axis becomes 0 and the signal level on the X axis becomes −1. In addition, in accordance with the orientation (inclination) of the mobile phone device 100, the acceleration sensor 20 generates and outputs axial acceleration signals showing signal levels in the range of ±1 in regard to each of the X axis, the Y axis, and the Z axis.

The filter 11 is a low-pass filter that removes frequency components equal to or greater than 200 Hz, for example, included in the axial acceleration signals on each of the X axis, the Y axis, and the Z axis from the acceleration sensor 20. There are cases where the carrier P of the mobile phone device 100 views images displayed on the monitor screen S while walking or running, for example. During movement such as walking, the mobile phone device 100 oscillates or rotates in extremely short intervals up and down and right and left, so high frequency components become included in the axial acceleration signals. If the direction in which the images are displayed is switched based on axial acceleration signals including high frequency components, the direction in which the images are displayed frequently switches and it becomes hard to view the images, so the high frequency components are removed to avoid this. It will be noted that although in this embodiment a configuration where the filter 11 is built into the traveling direction determination device 10 is described as an example, the filter 11 is not limited to this and may also be realized with software by the microprocessor or may also be provided outside the traveling direction determination device 10.

The acceleration data importation unit 12 imports, as axial acceleration data streams comprising axial acceleration data obtained by sampling at predetermined sampling intervals, the axial acceleration signals in regard to each of the X axis, the Y axis, and the Z axis from which the high frequency components have been removed by the filter 11. In other words, the acceleration data importation unit 12 obtains acceleration data streams in regard to each axis by sampling, at the predetermined sampling intervals, instantaneous values of acceleration on each axis. Here, the axial acceleration data indicate, as data values in the range of ±1 for example, the magnitude and the direction of acceleration at the importation points in time. Namely, ± indicates the direction of acceleration, and the absolute value of the data value indicates the magnitude of acceleration. The axial acceleration data streams are data streams comprising plural sets of axial acceleration data.

The sampling intervals at which the acceleration data importation unit 12 acquires the axial acceleration data streams can be appropriately set in accordance with the use and function of the device mounted with the traveling direction determination device 10. For example, in a case where the traveling direction determination device 10 is mounted in the mobile phone device 100 and shared with a pedometer, the carrier P walks while carrying the mobile phone device 100, so the sampling intervals are set based on the walking pace. Assuming, for example, that the maximum frequency of walking is 4 Hz, the interval of one step becomes 250 milliseconds, so the acceleration data importation unit 12 acquires the axial acceleration data streams in shorter intervals than this. To more accurately measure the number of steps, it is preferred that the number of steps be measured by detecting changes in acceleration at several points in time during the motion of walking one step. For that reason, when, for example, measuring the number of steps by detecting, at four points, changes in acceleration during the motion of one step, it is necessary to acquire the axial acceleration data streams at intervals of 62.5 milliseconds, and by measuring the number of steps in even shorter intervals, more changes in acceleration per step can be acquired, so a more accurate step count can be measured, and measuring the number of steps at 30-millisecond intervals is ideal.

The first determination unit 13 selects a gravity axis closest to the gravity direction of the moving object based on the axial acceleration data streams of each of the X axis, the Y axis, and the Z axis acquired by the acceleration data importation unit 12 to determine the gravity direction of the moving object. The first determination unit 13 compares (hereinafter sometimes called an "acceleration comparison") to one another the magnitudes of acceleration represented by the axial acceleration data of each of the X axis, the Y axis, and the Z axis from the acceleration data importation unit 12 and selects any one of these axes as the gravity axis. The first determination unit 13 selects the gravity axis based on the result of at least one acceleration comparison. However, the number of acceleration comparisons for selecting the gravity axis is not limited to this and may be freely set.

In a case where the first determination unit 13 is set to select the gravity axis based on the result of one acceleration comparison, the first determination unit 13 compares to one another the absolute value of acceleration on the X axis represented by the X axis acceleration data, the absolute value of acceleration on the Y axis represented by the Y axis acceleration data, and the absolute value of acceleration on the Z axis represented by the Z axis acceleration data from the acceleration data importation unit 12 in the same timeframe and selects, as the gravity axis, the axis corresponding to the acceleration with the largest absolute value. For example, if the magnitudes of acceleration represented by the axial acceleration data from the acceleration data importation unit 12 are –0.99 on the X axis, 0.05 on the Y axis, and 0.07 on the Z axis, the first determination unit 13 selects the X axis, which has the largest absolute value, as the gravity axis to determine the gravity direction of the moving object.

In a case where the first determination unit 13 is set to select the gravity axis based on the result of plural acceleration comparisons, the first determination unit 13 compares to one another the X axis acceleration data stream, the Y axis acceleration data stream, and the Z axis acceleration data stream from the acceleration data importation unit 12 in a predetermined determination period and selects, as the gravity axis, any one of the X axis, the Y axis, and the Z axis. More specifically, in a case where the first determination unit 13 has determined, in a predetermined number of determinations over time, that the absolute value of acceleration in regard to any one of the X axis, the Y axis, and the Z axis is greater than the absolute values of acceleration on the other axes in a predetermined determination period, the first determination unit 13 selects that one axis as the gravity axis to determine the gravity direction of the moving object.

The second determination unit 14 uses the gravity axis selected by the first determination unit 13 to determine the traveling direction of the carrier P. The traveling direction of the carrier P is generally difficult to determine because it also depends how (orientation, inclination, etc.) the carrier P is holding the mobile phone device 100. The second determination unit 14 pertaining to this embodiment determines the traveling direction in consideration of the gravity axis selected in the first determination unit 13 but also takes into account the following observations about people's behavior. Here, it will be assumed that the carrier P is carrying the mobile phone device 100 in a clothing pocket or the like as shown in FIG. 1B<3>.

That is, it has been observed that the motions of the carrier P carrying the mobile phone device 100 have the following tendency.

People often tilt their bodies forward because in terms of body structure it is easy to bend forward. Namely, in daily life, motions in which people bend their bodies forward tend to be greater, and their frequency tends to be higher, than motions in which people bend (tilt) their bodies leftward, rightward, or rearward. This embodiment utilizes this characteristic of people's behavior. Specific examples of motions in which people bend their bodies forward can include the following kinds of motions.

Figure 1C:
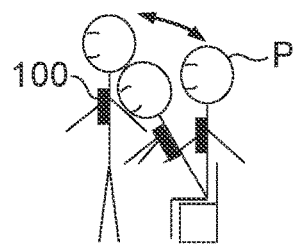
FIG. 1C is a drawing describing characteristics in a person's motions pertaining to the embodiment.
Figure 1C:
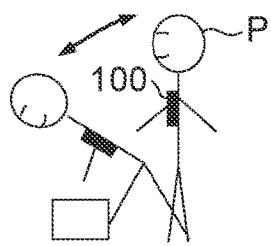
Figure 1C:
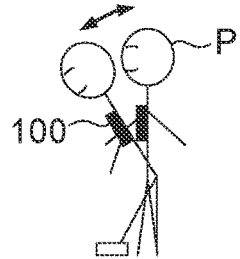

[Motion 1] A motion when a person stands up from a chair and sits down in a chair such as shown in FIG. 1C<1>.

[Motion 2] A motion when a person picks up an object on the floor such as shown in FIG. 1C<2>.

[Motion 3] A motion when a person slips on shoes while standing such as shown in FIG. 1C<3>.

For example, when the carrier P performs the above motions in a case where the carrier P has put the mobile phone device 100 in a chest pocket, the axis closest to the forward-facing direction of the carrier P of the two axes excluding the gravity axis selected by the first determination unit 13 changes greatly. The second determination unit 14 selects the direction of the mobile phone device 100 closest to the forward-facing direction of the carrier P from this change to determine the traveling direction of the carrier P.

Next, the procedural steps in the traveling direction determination (hereinafter sometimes called the "traveling direction determination process") executed in the traveling direction determination device 10 pertaining to this embodiment will be described. The specific procedural steps in the traveling direction determination process pertaining to this embodiment are as follows.

[Procedural Step 1] Determine gravity direction. This determination is performed by the first determination unit 13.

The values on each axis of the acceleration sensor 20 are low-pass filtered by the filter 11. As described above, the first determination unit 13 selects, as the gravity axis, the axis corresponding to the value with the largest absolute value among the acceleration signals on the X axis, the Y axis, and the Z axis after the filtering, and also determines the polarity by the "+" or "–" sign on that axis to determine the gravity direction.

[Procedural Step 2] Determine traveling direction. This determination is performed by the second determination unit 14.

The second determination unit 14 selects the axis in which the absolute value of the difference between the current value (hereinafter sometimes called "the current value") of the acceleration signal on each axis and the moving average value is the larger among the two axes excluding the gravity axis selected in procedural step 1. The second determination unit 14 handles the selected axis as the axis (hereinafter sometimes called the "travel axis") of the mobile phone device 100 closest to the traveling direction of the carrier P. Moreover, the second determination unit 14 judges, by whether or not the sign of the travel axis (current value–moving average value) is "+" or "–", whether the direction of that axis is the plus direction or the minus direction and selects the direction of the mobile phone device 100 closest to the traveling direction of the carrier P. The direction of the mobile phone device 100 is selected among any of the six directions of X+, X–, Y+, Y–, Z+, and Z–, and the direction of the mobile phone device 100 that has been selected is determined to be the traveling direction of the carrier P. The traveling direction that has been determined is output as a detection signal from the traveling direction determination device 10.

It will be noted that when the second determination unit 14 determines, as the travel axis, the axis corresponding to the value in which the absolute value of the difference between the current value and the moving average value is the larger in "procedural step 2," the second determination unit 14 may also add the frequency with the largest absolute value and determines the axis with the highest frequency as the travel axis. Furthermore, in order to judge inclination as accurately as possible when determining the traveling direction, the second determination unit 14 may also check that the value (the resultant value, the square root of the sum of squares of the value of each axis) of the resultant vector of the acceleration signals on the X axis, the Y axis, and the Z axis (hereinafter sometimes called "resultant vector") is within an allowable range with respect to the average value. Moreover, in a case where the gravity axis selected by the first determination unit 13 has changed, there is the potential that the carrier P has changed the location or the direction in which the mobile phone device 100 is being carried, so the traveling direction determination device 10 may redo the determinations from procedural step 1.

Next, examples of traveling direction determinations that have actually been performed will be described with reference to FIG. 2A to FIG. 2C and FIG. 4A and FIG. 4B.

Figure 2A:
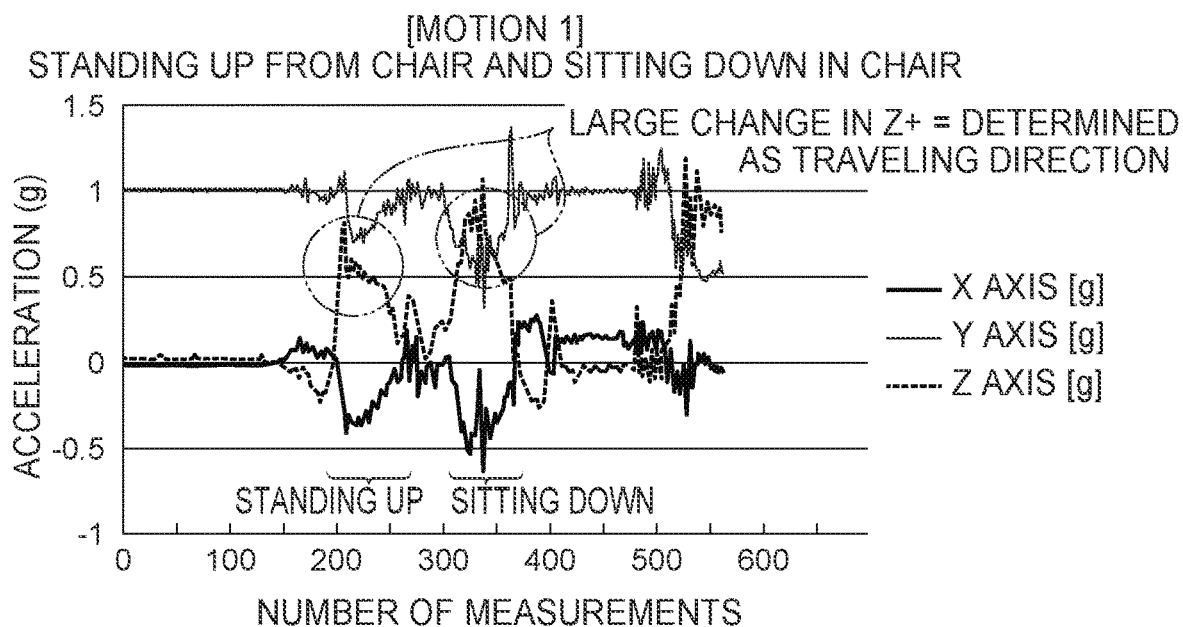
FIG. 2A is a graph showing acceleration signals of motions when a person carrying the mobile device mounted with the acceleration sensor stands up from a chair and sits down in the chair.
Figure 2B:
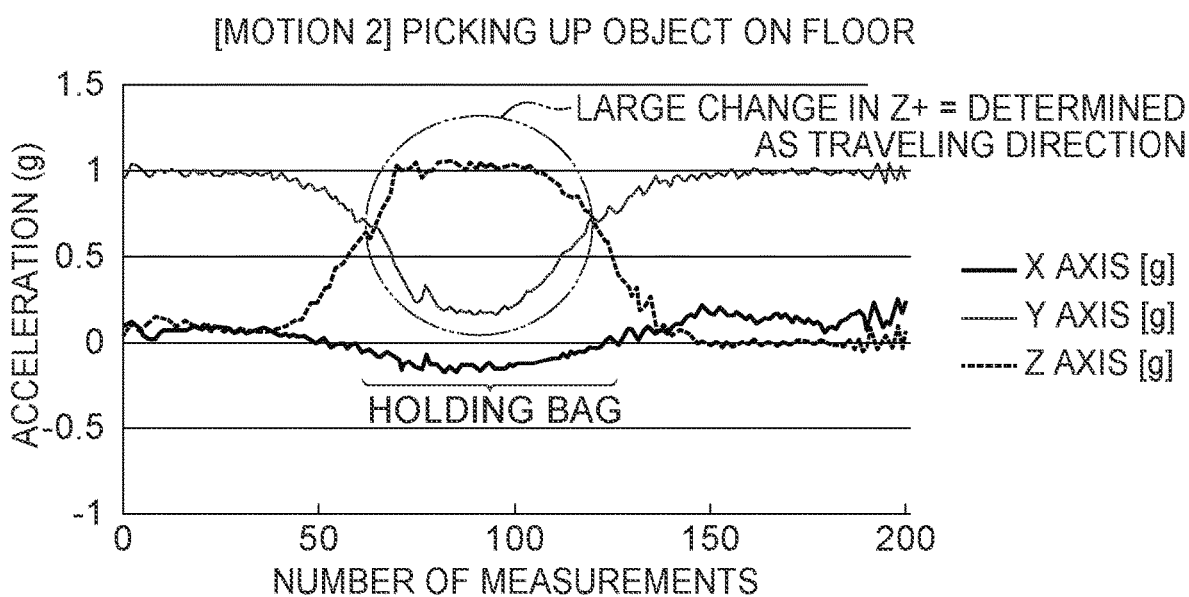
FIG. 2B is a graph showing acceleration signals of motions when the person carrying the mobile device mounted with the acceleration sensor picks up an object on a floor.

FIG. 2A to FIG. 2C are graphs showing traveling direction determination results in cases where each of "motion 1" to "motion 3" have been performed. FIG. 2A shows determination results of "motion 1." FIG. 2B shows determination results of "motion 2." FIG. 2C shows determination results of "motion 3." The positional relationship between the mobile phone device 100 and the acceleration sensor 20 and the carried state of the mobile phone device 100 at the acquisition times in the graphs shown in FIG. 2A to FIG. 2C are as shown in FIG. 1B. FIG. 2A to FIG. 2C each show results obtained by sampling, at the predetermined sampling intervals (in these examples, 30 ms), the acceleration signals on the X axis, the Y axis, and the Z axis output from the acceleration sensor 20 in accompaniment with each motion, with the horizontal axis indicating the number of samples and the vertical axis indicating the magnitude of acceleration. When the acceleration value is positive, the acceleration shows a "+" direction, and when the acceleration value is negative, the acceleration shows a "−" direction. It will be noted that in FIG. 2A to FIG. 2C the "Y+" direction is determined beforehand as the gravity direction. Consequently, the direction of the mobile phone device 100 closest to the traveling direction of the carrier P becomes either the X axis direction (X+ or X−) or the Z axis direction (Z+ or Z−).

FIG. 2A shows the acceleration signals on each axis when the carrier P has performed the motion of standing up from a chair and thereafter sitting down in the chair as "motion 1." It will be understood that two peaks occur in the values of the acceleration signals on each axis in accompaniment with each motion. As shown in FIG. 2A, the acceleration signal on the X axis also swings between positive and negative from 0 due to the change in posture associated with the motion, but the change in absolute value is greatest on the Z axis. Consequently, the Z axis is selected as the travel axis. Moreover, the sign of the acceleration signal on the Z axis is positive (the value is greater than 0), so the direction of the mobile phone device 100 closest to the traveling direction of the carrier P is selected to be the Z+ direction, and the traveling direction is determined to be the Z+ direction.

FIG. 2B shows the acceleration signals on each axis when the carrier P has performed the motion of picking up an object on the floor as "motion 2." It will be understood that the values of the acceleration signals on each axis change in accompaniment with each motion. As shown in FIG. 2B, the acceleration signal on the X axis also swings between positive and negative from 0 due to the change in posture associated with the motion, but the change in absolute value is greatest on the Z axis. Consequently, the Z axis is selected as the travel axis. Moreover, the sign of the acceleration signal on the Z axis is positive (the value is greater than 0), so the direction of the mobile phone device 100 closest to the traveling direction of the carrier P is selected to be the Z+ direction, and the traveling direction is determined to be the Z+ direction.

FIG. 2C shows the acceleration signals on each axis when the carrier P has performed the motion of slipping on shoes while standing as "motion 3." It will be understood that the values of the acceleration signals on each axis change in accordance with each motion. As shown in FIG. 2C, the acceleration signal on the X axis also swings between positive and negative from 0 due to the change in posture associated with the motion, but the change in absolute value is greatest on the Z axis. Consequently, the Z axis is selected as the travel axis. Moreover, the sign of the acceleration signal on the Z axis is positive (the value is greater than 0), so the direction of the mobile phone device 100 closest to the traveling direction of the carrier P is selected to be the Z+ direction, and the traveling direction is determined to be the Z+ direction.

From the results shown in FIG. 2A to FIG. 2C, it will be understood that the premise of the traveling direction determination process pertaining to this embodiment according to the above-described procedural steps is valid. The "traveling direction of the carrier P" in this embodiment refers to the direction of the mobile phone device 100 closest to the actual traveling direction of the carrier P, and there are also cases where the actual traveling direction the carrier P coincides with the direction of the mobile phone device 100. Furthermore, the "traveling direction" pertaining to this embodiment also includes directions with a high probability of being the traveling direction in a case where the carrier P performs a certain motion even though the carrier P has not yet traveled and thereafter travels as a next motion.

Figure 3:
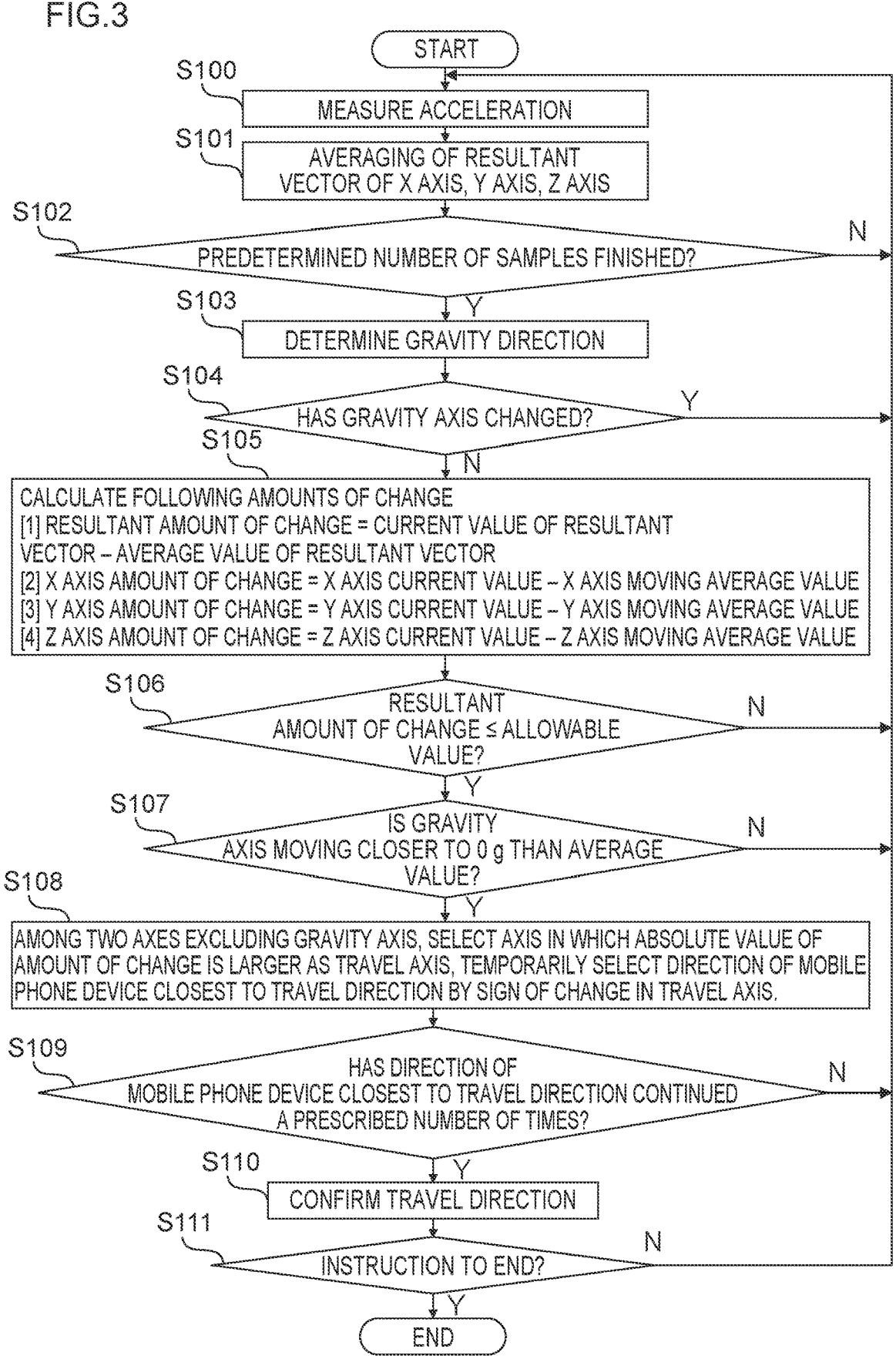
FIG. 3 is a flowchart showing the flow of a traveling direction determination process executed by the traveling direction determination device pertaining to the embodiment.

Next, the traveling direction determination process executed in the traveling direction determination device 10 pertaining to this embodiment will be described with reference to FIG. 3. FIG. 3 is a flowchart showing a flow of processes in a traveling direction determination processing program executed in the traveling direction determination process. The traveling direction determination processing program may be configured to be executed by the microprocessor that realizes the traveling direction determination device 10 or may be configured to be executed by a control unit of the mobile phone device 100 mounted with the traveling direction determination device 10. In any event, the traveling direction determination processing program is stored in storage means such as a ROM not shown in the drawings, and upon receiving via a user interface (e.g., the monitor screen S of the mobile phone device 100) or the like an instruction to start executing the program, a CPU not shown in the drawings reads the traveling direction determination processing program from the storage means such as the ROM, transfers it to a RAM or the like, and executes it.

In step S100, the CPU receives the acceleration signals from the acceleration sensor 20 and starts measuring acceleration. In this embodiment, the CPU performs the measurement by sampling the acceleration signals at 30-ms intervals.

In step S101, the CPU executes an averaging process that calculates the moving average values of acceleration on each of the X axis, the Y axis, and the Z axis and the average value of the resultant value of the resultant vector.

In step S102, the CPU determines whether or not predetermined number of samples has ended. When the determination is YES, the CPU moves to the next step S103, and when the determination is NO, the CPU returns to step S100 and continues the sampling.

In step S103, the CPU determines the gravity direction by the procedural step described above.

In the next step S104, the CPU determines whether or not the gravity axis selected in step S103 has changed. The CPU performs this determination based on whether or not the axis corresponding to the value with the largest absolute value among the acceleration signals on the X axis, the Y axis, and the Z axis has changed. When the determination is YES, the CPU returns to step S100 and continues the sampling. It will be noted that, as described above, this step is not an essential process and may be omitted.

In step S105, the CPU calculates amounts of change from average values of the following parameters.

Resultant amount of change=current value of resultant vector−average value of resultant vector  [1]

Amount of change on X axis=current value on X axis−moving average value on X axis  [2]

Amount of change on Y axis=current value on Y axis−moving average value on Y axis  [3]

Amount of change on Z axis=current value on Z axis−moving average value on Z axis  [4]

The CPU calculates the moving average values by predetermining the number of samples (rate) in which the moving average is taken. It will be noted that the amounts of change calculated in this step are absolute values. Furthermore, in this step, the CPU uses the moving average values as reference values of the amounts of change in the acceleration signals on each axis, but the CPU is not limited to this and may also use other forms of average values or values serving as references.

Figure 4A:
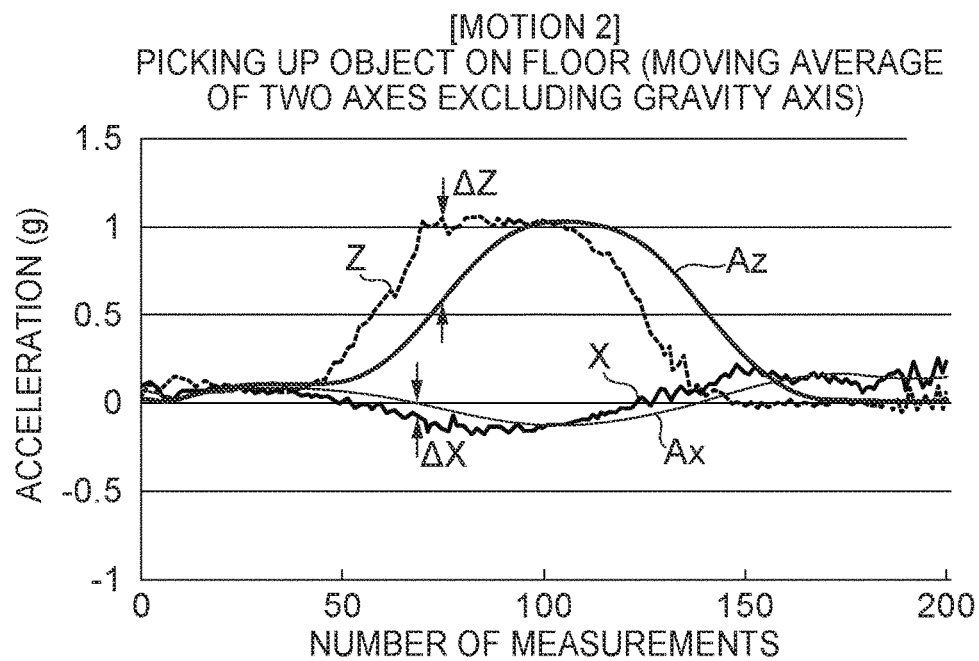
FIG. 4A is a graph describing the relationship between the output of the acceleration sensor and moving average values.

Here, the amounts of change on each axis will be more specifically described with reference to FIG. 4A. FIG. 4A shows an example in the case of "motion 2," and shows the relationship between a current value X and a moving average value Ax of the X axis and the relationship between a current value Z and a moving average value Az of the Z axis. In this case, the amount of change on the X axis is ΔX shown in FIG. 4A, and the amount of change on the Z axis is ΔZ. In the example shown in FIG. 4A, regarding ΔZ, ΔX in a predetermined time (timing), |ΔZ|>|ΔX|, so the Z axis is selected as the travel axis. In this way, in this embodiment, the moving average values serve as reference values for calculating the amounts of change on each axis. It will be noted that in FIG. 4A, the sampling rate of the moving averages is, for example, 32 times.

In step S106, the CPU determines whether or not the resultant amount of change calculated in step S105 falls within the range of a predetermined allowable value. When the determination is YES, the CPU moves to step S107, and when the determination is NO, the CPU returns to step S100. The value of the allowable value is not particularly limited and is appropriately set in consideration of the precision of the traveling direction determination device, for example. In this embodiment, as an example, the allowable value set to 0.2 g.

Figure 4B:
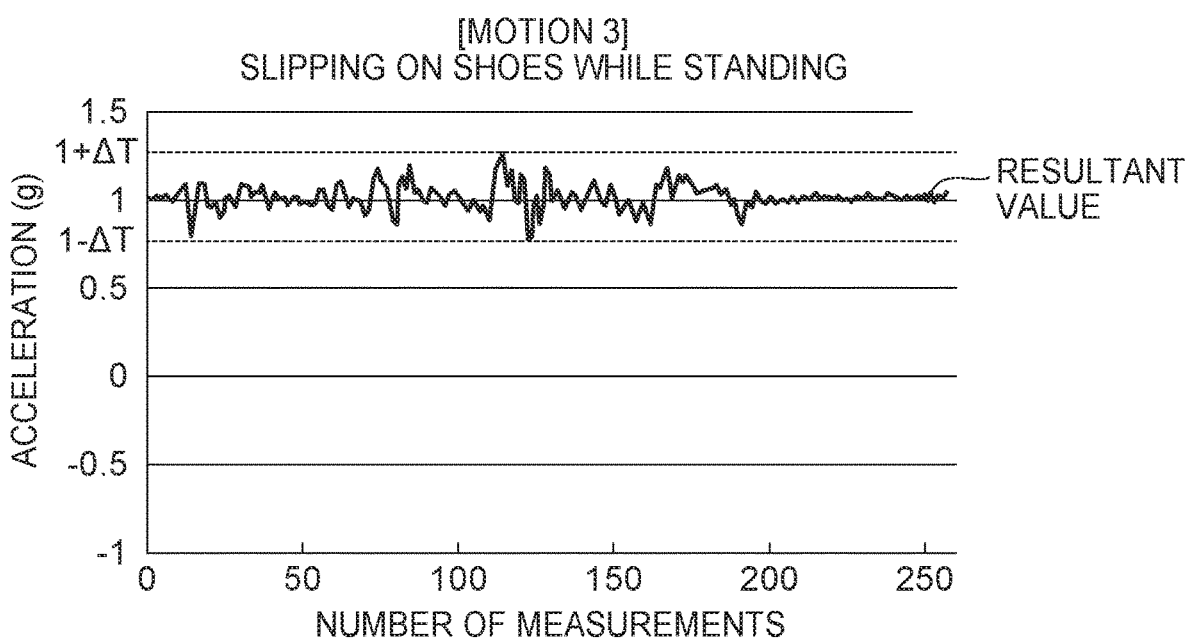
FIG. 4B is a graph describing fluctuations in a resultant vector.

Here, the resultant amount of change will be described in greater detail with reference to FIG. 4B. FIG. 4B shows an example in the case of "motion 3," and shows fluctuations in the resultant value. As shown in FIG. 4B, the resultant value changes in positive and negative directions centered on an average value of 1 for example. In this case an allowable value ΔT is set in positive and negative directions centered on "1." Namely, if the absolute value of the resultant amount of change is less than or equal to ΔT, the determination in step S106 becomes YES, and if the absolute value of the resultant amount of change is greater than ΔT, the determination in step S106 becomes NO. The point of step S106 is to exclude unforeseen behavior, such as the carrier P suddenly starting to run, and as mentioned above is not an essential process.

In step S107, the CPU determines whether or not the gravity axis selected in step S103 is moving closer in the direction of 0 g than the average value. The CPU performs this determination by, for example, setting a threshold value with respect to a divergence amount, which is the absolute value of the difference between the average value and the current value of the gravity axis selected in step S103, and determining whether or not the divergence amount is equal to or greater than the threshold value. That is, when the divergence amount is less than the threshold value, the determination becomes NO.

To describe this by way of the examples of FIG. 2A to FIG. 2C, the CPU determines whether or not the Y axis, which is the gravity axis, is moving closer to 0 g than the average value of 1 g. When the determination is YES, the CPU moves to the next step S108, and when the determination is NO, the CPU returns to step S100. This step is a process in which the CPU checks that the value of the gravity axis (in the examples of FIG. 2A to FIG. 2C, the Y axis) is tending to decrease (become closer to 0) when the value of the travel axis (in the examples of FIG. 2A to FIG. 2C, the Z axis) increases as shown in FIG. 2A to FIG. 2C. For example, there are cases where the value of the gravity axis does not decrease even if the value of the travel axis increases in a state in which an additional force has acted on the acceleration sensor, such as, for example, the carrier P shaking the acceleration sensor while holding it in hand. Consequently, step S107 is a process for checking whether or not the gravity axis has been measured in a state in which an abnormal external force has acted, and may also be omitted.

In step S108, the CPU selects as the travel axis the axis in which the absolute value of the amount of change is the larger among the two axes excluding the gravity axis based on the procedural step described above, and temporarily selects the direction of the mobile phone device 100 closest to the traveling direction of the carrier P based on the sign of the change of the travel axis.

In step S109, the CPU determines whether or not the direction of the mobile phone device 100 closest to the traveling direction of the carrier P has continued a predetermined number of times. That is, the determination becomes NO when the number of times in which one direction has continuously been selected as the direction of the mobile phone device 100 closest to the traveling direction of the carrier P is less than the predetermined number of times. When the determination is YES, the CPU moves to step S110, and when the determination is NO, the CPU returns to step S100.

In step S110, the CPU confirms the selection of the direction of the mobile phone device 100 closest to the traveling direction of the carrier P to confirm the traveling direction.

In step S111, the CPU determines whether or not it has received an instruction to end the traveling direction determination processing program. When the determination is NO, the CPU returns to step S100, and when the determination is YES, the CPU ends the traveling direction determination processing program. The determination of whether or not the CPU has received an instruction to end the traveling direction determination processing program is, for example, performed by determining whether or not the carrier P has input, via the monitor screen S, an instruction to end the traveling direction determination processing program.

Here, in this embodiment, the processes from step S100 to step S104 are processes performed by the first determination unit 13, and the processes from step S108 to step S111 are processes performed by the second determination unit 14.

The processes from step S105 to step S107 may be executed by either the first determination unit 13 or the second determination unit 14, but in this embodiment they are performed by the second determination unit 14 as an example.

As described in detail above, according to the traveling direction determination device, the mobile device, and the traveling direction determination method pertaining to this embodiment, it becomes possible to easily determine, using the output of an acceleration sensor, the traveling direction of a moving object mounted with the acceleration sensor. That is, the traveling direction determination device, the mobile device, and the traveling direction determination method pertaining to this embodiment determine the traveling direction using only the acceleration sensor, can be realized with a simple configuration compared to a configuration using a dedicated system such as the global positioning system (GPS), and also contributes to reducing cost.

It will be noted that although in the above embodiment a configuration that determines the traveling direction using only the acceleration sensor was described as an example, in a case where the mobile phone device is mounted with a geomagnetic sensor and/or an angular velocity sensor for example, these sensors may also be used to assist in the determination of the traveling direction. Namely, correspondences between each axis of the acceleration sensor and each axis of the geomagnetic sensor or the angular velocity sensor are known at the point in time when the mobile phone device is manufactured, so the sensors can be used to assist in the determination of the traveling direction by correlation with the traveling direction (carried state) determined by the traveling direction determination device pertaining to this embodiment.

What is claimed is:

1. A traveling direction determination device that determines, using an acceleration sensor that generates acceleration signals indicating acceleration in three axial directions corresponding respectively to three axes, together with a direction of the acceleration, a traveling direction of a moving object mounted with the acceleration sensor, the traveling direction determination device comprising a determination unit that executes:
   a first determination process, in which the determination unit selects, using the acceleration signals, any of the three axes as a gravity axis, the gravity axis being closest to an actual gravity direction of the moving object to determine a gravity direction of the moving object; and
   a second determination process, in which the determination unit selects either of the two axes excluding the axis selected as the gravity axis, as a travel axis, the travel axis being closest to an actual traveling direction of the moving object based on moving average values of the acceleration signals, to determine the traveling direction of the moving object.

2. The traveling direction determination device of claim 1, wherein the determination unit executes the first determination process by selecting, as the gravity axis, an axis corresponding to an acceleration signal with a largest absolute value among the acceleration signals and determining the gravity direction by a sign of the acceleration signal corresponding to the gravity axis that was selected.

3. The traveling direction determination device of claim 1, wherein the determination unit executes the second determination process by selecting, as the travel axis, an axis in which an absolute value of a difference, between a current value of a corresponding acceleration signal at a predetermining timing and a moving average value over a predetermined number of times, is larger between the two axes excluding the gravity axis selected in the first determination process, and determining the traveling direction by a sign of the acceleration signal corresponding to the travel axis that was selected.

4. The traveling direction determination device of claim 1, wherein the determination unit executes the first determination process and the second determination process using the acceleration signals from the acceleration sensor in a case in which the moving object has performed a predetermined behavior.

5. The traveling direction determination device of claim 4, wherein in a case in which the moving object has performed the predetermined behavior, the determination unit re-executes the first determination process and the second determination process in a case in which a divergence amount, which is an absolute value of a difference between an average value and a current value for the acceleration signal on the gravity axis selected by the first determination process, is less than a predetermined value.

6. The traveling direction determination device of claim 1, wherein the determination unit calculates an amount of change, from an average value, in a resultant vector obtained by vectorially combining the acceleration signals in the three axial directions, and re-executes the first determination process and the second determination process in a case in which the amount of change is outside a predetermined range centered on the average value.

7. The traveling direction determination device of claim 1, wherein the determination unit re-executes the first determination process and the second determination process in a case in which a number of times in which one direction has been continuously determined as the traveling direction in the second determination process is less than a predetermined number of times.

8. A mobile device comprising:
   an acceleration sensor that generates acceleration signals indicating acceleration in three axial directions together with a direction of the acceleration; and
   the traveling direction determination device of claim 1.

9. A traveling direction determination method that determines, using an acceleration sensor that generates acceleration signals indicating acceleration in three axial directions corresponding respectively to three axes, together with a direction of the acceleration, a traveling direction of a moving object mounted with the acceleration sensor, the traveling direction determination method comprising:
   a first step of selecting, using the acceleration signals from the acceleration sensor in a case in which the moving object has performed a predetermined behavior, any of the three axes as a gravity axis to determine a gravity direction of the moving object; and
   a second step of selecting, as a travel axis based on moving average values of the acceleration signals, either of the two axes excluding the gravity axis, to determine the traveling direction of the moving object.

* * * * *